United States Patent [19]

Kimura et al.

[11] Patent Number: 5,077,048
[45] Date of Patent: Dec. 31, 1991

[54] BOWEL LAVAGE COMPOSITION

[75] Inventors: Isami Kimura; Akemi Kamiya, both of Shiga; Sumihiro Shiraishi, Otsu; Makoto Sato, Moriyama, all of Japan

[73] Assignee: Morishita Pharmaceutical Co., Ltd., Osaka, Japan

[21] Appl. No.: 464,522

[22] Filed: Jan. 12, 1990

[51] Int. Cl.$^5$ ............................................. A61K 9/08
[52] U.S. Cl. .................................. 424/422; 424/400; 424/439; 514/892
[58] Field of Search ................. 424/422, 400, 439; 514/892

[56] References Cited

U.S. PATENT DOCUMENTS 3,211,614 10/1965 Embring et al. ..................... 167/56
3,495,010 2/1970 Fossel et al. ........................ 514/547

FOREIGN PATENT DOCUMENTS

87/00754 2/1987 World Int. Prop. O. .

OTHER PUBLICATIONS

J. Hewitt et al., "Whole-Gut Irrigation in Preparation for Large-Bowel Surgery", The Lancet, vol. 2, (1973), pp. 337-340.
Marc-Andre Bigard et al., "Fatal Colonic Explosion During Colonoscopic Polypectomy", Gastroenterology, vol. 77 (1979) pp. 1307-1310.
G. R. Davis et al., "Development of a Lavage Solution Associated with Minimal Water and Electrolyte Absorption or Secretion", Gastroenterology, vol. 78 (1980), pp. 991-995.
Int'l. Advances in Surg. Oncology, 6:257-270 (1983), Keighley et al., "Indications and Techniques for Bowell Preparation in Colorectal Cancer".
Gastroenterology, vol. 78, No. 5, May 1980, Davis et al., "Development of a Lavage Solution Associated with Minimal Water and Electrolyte Absorption or Secretion".

Primary Examiner—Thurman K. Page
Assistant Examiner—James M. Spear
Attorney, Agent, or Firm—Wegner, Cantor, Mueller & Player

[57] ABSTRACT

A bowel lavage composition which comprises one or more of a water-soluble polymer selected from the group consisting of polyethylene glycol, dextran, dextrin, hydroxyethylated starch, polydextrose, arabic gum, pullulan and pectin; a sodium salt of an organic; a potassium salt of an organic acid; sodium chloride; potassium chloride and sodium sulfate, having the following formulation:

| Water-soluble polymer | 10-150 g |
|---|---|
| Sodium salt of an organic acid | 5-60 mmol |
| Potassium salt of an organic acid | 0-12 mmol |
| Sodium chloride | 7-60 mmol |
| Potassium chloride | 0-12 mmol |
| Sodium sulfate | 0-20 mmol | wherein total potassium ion content in said composition ranges from 2 to 12 mEq. The bowel lavage composition is easily prepared in the form of the lavage solution when used, which is easily taken by patients, has reduced absorption of water, does not exert influence upon the electrolyte balance in living body with an excellent cleansing effect, does not contain hydrogen carbonate ion, and hence, is pharmaceutically stable and can be stored for a long period of time.

6 Claims, No Drawings

BOWEL LAVAGE COMPOSITION

The present invention relates to a bowel lavage composition which is used by dissolving in water.

PRIOR ART

Bowel cleansing is extremely important prior to accurate diagnosis in colonoscopy or double-contrast barium enema examination and for preventing infection after surgery of a lower intestine.

For such bowel cleansing, there has hitherto been employed a modified Brown method, which comprises administering a cathartic after dietary restriction with a low-residue diet or a liquid diet for several days and conducting a high enema with a large amount of warm water just before examination or surgery to cleanse the interior of colon. However, this method is time-consuming, painful for patients, and exerts a bad influence upon the electrolyte balance of body fluid and nutritional status.

It has been proposed a method comprising rapid ingestion of a large volume of a saline-based electrolyte solution and this method has been reported to be effective for pretreatment for colonoscopy [J. Hewitt et al., Lancet, 2, 337 (1973)].

However, this method is also painful for patients since patients must take a large volume of the electrolyte solution as much as 7 to 12 liters and further causes an absorption of a fairly large amount of sodium ion, chloride ion and water, and hence, this method cannot be applied to the patients with renal disease who are incapable of excreting salts or water or to the aged patients.

Thereafter, a balanced electrolyte solution (hereinafter referred to as "BES") comprising sodium chloride, potassium chloride and sodium hydrogen carbonate has been proposed in order to keep normal electrolyte balance in the living body. Although this BES does not affect the electrolyte balance in the living body so much, it is accompanied with an absorption of a fairly large volume of water.

In order to reduce such an absorption of water, an electrolyte composition supplemented with mannitol as an osmotically active agent has been proposed and confirmed to be effective. However, it is reported that mannitol in the composition is degraded by colonic bacteria to generate hydrogen gas and thereby an explosion accident in the large intestine was observed during polypectomy of the large intestine [M.A. Bigard et al Gastroenterology, 77, 1307 (1979)].

Davis et al. have proposed an electrolyte composition employing poorly absorbable polyethylene glycol in place of mannitol as an osmotically active agent. They have further proposed a unique electrolyte composition (commercially available as "Golytely") where a part of sodium chloride in the electrolyte composition is replaced with sodium sulfate in order to inhibit an absorption of sodium ion and confirmed to be useful [G.R. Davis et al., Gastroenterology, 78, 991 (1980)].

However, this Golytely has a bitter taste due to a large amount of sodium sulfate contained therein, and hence, it is not suitable for use in such a large amount as for intestinal washing.

Another unique electrolyte composition has been proposed which is prepared by removing sodium sulfate from the Golytely electrolyte composition, instead increasing the amount of polyethylene glycol and adjusting the osmotic pressure to isotonic (WO 87/00754).

It has been described in said literature that this lavage solution has less bitter taste and reduced absorption of water and electrolyte ions. However, when compared with Golytely, the lavage solution gives a clammy feeling when used due to higher concentration of polyethylene glycol and it is expected that sodium ion in the living body is excreted since the lavage solution contains lower concentration of sodium ion, which exerts a bad influence upon the electrolyte balance in the living body. The lavage solution is further disadvantageous in that it is pharmaceutically instable due to hydrogen carbonate ion contained therein and hence required for preparation when used and there is required much time to dissolve a large amount of polyethylene glycol.

SUMMARY OF THE INVENTION

In order to solve the above-mentioned problems, the present inventors have firstly studied the action, effect and necessity of each component used in the conventional bowel lavage composition in dogs and rats and then have intensively studied as to use of other components which have hitherto never been used for a bowel lavage composition.

As a result, it has been found that the blood pH is apparently affected by the hydrogen carbonate ion level in the bowel lavage composition, that the blood pH is never affected by an organic acid ion when it is used in place of the hydrogen carbonate ion, that a potassium ion level which does not affect the electrolyte balance in the living body is preferably in such a small range as 2 to 12 mEq/liter, that a chloride ion level is preferably in the range of from 7 to 60 mEq/liter, and that it is preferable to adjust the osmotic pressure of the aqueous solution to the preferred range of from 270 to 350 mOsm with sodium ion, an organic acid ion and a water-soluble polymer.

The object of the present invention is to provide a bowel lavage composition which can easily be taken by patients, shows reduced absorption of water, does not exert a bad influence upon the electrolyte balance in the living body and shows an excellent cleansing effect.

The present invention concerns a bowel lavage composition which comprises one or more of a water-soluble polymer selected from the group consisting of polyethylene glycol, dextran, dextrin, hydroxyethylated starch, polydextrose, arabic gum, pullulan and pectin; a sodium salt of an organic acid; a potassium salt of an organic acid; sodium chloride; potassium chloride and sodium sulfate, having the following formulation:

| Water-soluble polymer | 10–150 g |
| Sodium salt of an organic acid | 5–60 mmol |
| Potassium salt of an organic acid | 0–12 mmol |
| Sodium chloride | 7–60 mmol |
| Potassium chloride | 0–12 mmol |
| Sodium sulfate | 0–20 mmol | wherein total potassium ion content in said composition ranges from 2 to 12 mEq.

The most preferable water-soluble polymer is polyethylene glycol 4000 (Japanese Pharmacopoeia).

The organic acid suitable for the above sodium salt and potassium salt thereof includes acetic acid, lactic acid, citric acid, succinic acid, malic acid, tartaric acid, etc. but the present invention is not limited thereto.

Among these organic acids, citric acid is most preferable.

Preferred formulation of the bowel lavage composition of the present invention using preferred components is a follows:

| Polyethylene glycol 4000 | 50–120 g |
|---|---|
| Sodium citrate | 20–60 mmol |
| Sodium chloride | 20–50 mmol |
| Potassium chloride | 4–12 mmol |
| Sodium sulfate | 0–20 mmol |

The bowel lavage composition of the present invention can be prepared in the following manner. Firstly, each component is pulverized into fine powder with a pulverizer and then sieved. Then, each component of the above formulation is uniformly mixed with each other using a mixer and then divided into a suitable unit composition with a dividing machine, such as for 1 liter, 2 liter, 3 liter or 4 liter lavage solution.

The lavage solution of the present invention can be prepared in accordance with a usual procedure of preparing transfusions. The concentration of the intestinal washing solution can optionally be selected ranging from about 4 times higher concentration than that of an isotonic solution to a nearly isotonic concentration (osmotic pressure, around 290 mOsm/liter) in accordance with the dilution ratio when used.

The bowel lavage composition of the present invention may also contain sweetening, spice and the like if necessary.

The bowel lavage composition of the present invention allows for easy preparation of the lavage solution when used. The lavage solution of the present invention is easily taken by patients, has reduced absorption of water, does not exert influence upon the electrolyte balance in the living body and shows an excellent cleansing effect. Further, the lavage solution of the present invention does not contain hydrogen carbonate ion, and hence, is pharmaceutically stable and can be stored for a long period of time, which saves time for preparation when used.

The present invention is illustrated by the following Examples and Experiments, but should not be construed to be limited thereto.

EXAMPLE 1

Sodium chloride (Japanese Pharmacopoeia), potassium chloride (Japanese Pharmacopoeia) and sodium citrate (Japanese Pharmacopoeia) were sieved with a sieve of 500 μm screen diameter. Sodium chloride (35.0 kg), potassium chloride (22.4 kg) and sodium citrate (309 kg), sieved as mentioned above, were put in a VI-500 Mixer (manufactured by Tokuju Kosakusho K.K.) and the mixture was blended for 20 minutes to prepare mixed electrolyte powder. Paraffin-like polyethylene glycol 4000 (Japanese Pharmacopoeia) was pulverized with a Pinmil Pulverizer (manufactured by Nara Kikai K.K.) and then sieved with a sieve of 500 μm screen diameter to prepare pulverized polyethylene glycol 4000.

The above pulverized polyethylene glycol 4000 (225 kg) and the above mixed electrolyte powder (36.6 kg) were put in a VI-500 Mixer and the mixture was blended for 20 minutes to give a uniform mixture. The resulting mixed powder was filled in an aluminum bag made of polyester, polyethylene and aluminum foil using an automatic quantitative bag-filling machine FA-400 (manufactured by Yamato Seiko K.K.) to give 1200 bags of bowel lavage composition (for 2 liter) with each bag containing 174.4 g of the composition. The content of the composition in each bag can be varied if necessary.

EXAMPLE 2

The mixed electrolyte powder (36.6 kg) prepared as in Example 1 and polydextrose (225 kg) were put in VI-500 Mixer and the mixture was blended for 30 minutes to give a uniform mixed powder. Using this mixed powder (210 kg), the procedure of Example 1 was repeated to give 1200 bags of the bowel lavage composition containing each 174.4 g of the mixed powder.

EXAMPLES 3 TO 11

The procedure of Example 1 was repeated to give the bowel lavage compositions (for 2 liter) having the formulation as shown in Table 1.

TABLE 1

| Component (g) | Example No. | | | | | | | | |
|---|---|---|---|---|---|---|---|---|---|
| | 3 | 4 | 5 | 6 | 7 | 8 | 9 | 10 | 11 |
| Polyethylene glycol 4000 | 220 | 180 | 180 | 170 | 140 | 120 | 0 | 0 | 140 |
| Dextran 40 | 0 | 0 | 0 | 0 | 0 | 0 | 440 | 440 | 0 |
| Hydroxyethylated starch | 0 | 0 | 0 | 0 | 0 | 0 | 0 | 0 | 0 |
| Sodium citrate | 5.88 | 11.8 | 11.8 | 14.7 | 17.6 | 20.6 | 20.6 | 20.6 | 11.8 |
| Sodium chloride | 2.34 | 2.92 | 3.50 | 3.50 | 4.09 | 4.67 | 2.34 | 2.34 | 2.92 |
| Potassium chloride | 1.49 | 1.49 | 1.49 | 1.49 | 1.49 | 1.49 | 1.49 | 1.49 | 1.49 |
| Sodium sulfate | 0 | 0 | 0 | 0 | 0 | 0 | 0 | 0 | 5.68 |

EXAMPLE 12

A 100 liter dissolving vessel equipped with a stirrer was charged with polyethylene glycol 4000 (7500 g), sodium chloride (117 g), potassium chloride (74.6 g) and sodium citrate (Japanese Pharmacopoeia; 1030 g) and thereto was added distilled water while stirring to dissolve the mixture so that the total amount of the mixture became 100 liters. Each 2 liters of this solution was poured into vessels made of a synthetic resin to give 50 lavage solutions (for 2 liter).

In accordance with the above procedure, the conventional lavage solutions BES, Golytely and physiological saline were prepared for use in the following Experiments. Table 2 shows the components (g) contained in each 2 liter of the lavage solutions.

TABLE 2

|  | BES | Golytely | PS* |
|---|---|---|---|
| Polyethylene glycol 4000 | 0 | 118 | 0 |
| Sodium hydrogencarbonate | 5.04 | 3.37 | 0 |
| Sodium chloride | 12.9 | 2.93 | 18.0 |
| Potassium chloride | 1.49 | 1.49 | 0 |
| Sodium sulfate | 0 | 11.4 | 0 |

(Note) PS: Physiological saline

Experiment 1 (Cleansing effect)

The lavage compositions (for 2 liter) prepared in Examples 1, 2, 3, 4, 8, 10 and 11 were dissolved in distilled water to give the lavage solutions having the total amount of 2 liters. These lavage solutions and Golytely were tested for their cleansing effect in rats.

Male SD rats 8 to 10 weeks old, which have been fasted for 24 hours, were divided into 5 animals in each group. Each 20 ml/kg of the lavage solutions of the present invention and Golytely were orally administered to the animals for 15 times with 10 minutes interval. Ten minutes after the last administration, whole intestinal contents from pyloric orifice to rectum were obtained and the dry weight thereof was measured. The results are shown in Table 3.

It was found that both the lavage solutions of the present invention and Golytely showed good cleansing effect.

TABLE 3

|  | Dry weight (mg) | Cleansing degree (%) |
|---|---|---|
| Control | 350 ± 41 | — |
| Ex. 1 | 111 ± 13 | 68.3 |
| Ex. 2 | 177 ± 20 | 49.4 |
| Ex. 3 | 177 ± 49 | 49.4 |
| Ex. 4 | 108 ± 19 | 69.1 |
| Ex. 8 | 127 ± 20 | 63.7 |
| Ex. 10 | 149 ± 23 | 57.4 |
| Ex. 11 | 125 ± 15 | 64.3 |
| Golytely | 137 ± 30 | 60.9 |

Experiment 2 (Effect on the intestinal electrolyte balance)

The lavage compositions (for 2 liter) prepared in Examples 1, 3, 4, 5, 6, 7, 8 and 11 were dissolved in distilled water to give the lavage solutions having the total amount of 2 liters. These lavage solutions and the above three kinds of solutions prepared in Example 12 (BES, Golytely and physiological saline) were tested for their effect on the intestinal electrolyte balance.

The test animals and the administration route were the same as those in Experiment 1. Ten minutes after the last administration, the intestinal contents in the colon were obtained and centrifuged. The supernatant was analyzed for the electrolyte concentration with a sodium-potassium automatic analyzer NOVA 1 (manufactured by Nova Biomedical) and a chloride counter CL-6MP (manufactured by Hiranuma). The results are shown in Table 4. It was found that the bowel lavage compositions of the present invention, BES and Golytely exerted substantially no influence upon the intestinal electrolyte balance.

TABLE 4

|  | Changes in intestinal electrolyte level (mM) | | |
|---|---|---|---|
|  | $Na^+$ | $K^+$ | $Cl^+$ |
| Ex. 1 | −3.8 | −1.59 | −17 |
| Ex. 3 | −9.2 | −5.32 | −13 |
| Ex. 4 | −5.6 | −3.49 | −19 |
| Ex. 5 | −12.4 | −4.00 | −23 |
| Ex. 6 | −7.1 | −2.12 | −21 |
| Ex. 7 | −7.7 | −2.12 | −26 |
| Ex. 8 | −10.6 | −1.01 | −31 |
| Ex. 11 | −11.1 | −2.01 | −23 |
| BES | −15.3 | −0.49 | −22 |
| Golytely | −8.9 | −2.12 | −28 |
| Physiological saline | −43.0 | +7.97 | −40 |

(Note): The symbols + and − show an increase and a decrease of the electrolyte levels from those in the original solutions, respectively.

Experiment 3 (Effect on the serum electrolyte balance)

The lavage compositions (for 2 liter) prepared in Examples 1 to 11 were dissolved in distilled water to give the lavage solutions having the total amount of 2 liters. These lavage solutions and the above three kinds of the solutions prepared in Example 12 (BES, Golytely and physiological saline) were tested for their effect on the serum electrolyte balance.

The test animals and the administration route were the same as those in Experiment 1. Ten minutes after the last administration, the animals were anesthetized with ether and blood was obtained from the abdominal aorta to measure the serum electrolyte level. The pH value and the hematocrit value which can be used as an index of waterabsorption were also measured. Table 5 shows the results of both serum electrolyte level and hematocrit value.

As clearly shown in Table 5, the lavage solutions of the present invention, BES, Golytely and physiological saline exerted substantially no influence upon serum electrolyte level, blood pH and hematocrit value.

TABLE 5

|  | Serum electrolyte level (mEq/liter) | | | | | Hematocrit |
|---|---|---|---|---|---|---|
|  | $Na^+$ | $K^+$ | $Cl^-$ | $HCO_3^-$ | pH | value (%) |
| Control | 148.8 ± 0.7 | 4.98 ± 0.12 | 108 ± 0 | 23.0 ± 0.4 | 7.43 | 42.3 ± 0.4 |
| Ex. 1 | 148.1 ± 1.3 | 5.11 ± 0.18 | 106 ± 1 | 28.6 ± 0.9 | 7.48 | 42.0 ± 0.7 |
| Ex. 2 | 148.7 ± 0.5 | 4.87 ± 0.15 | 110 ± 1 | 25.6 ± 0.9 | 7.46 | 42.6 ± 0.8 |
| Ex. 3 | 148.0 ± 1.2 | 5.05 ± 0.07 | 108 ± 1 | 25.7 ± 0.8 | 7.44 | 43.3 ± 0.7 |
| Ex. 4 | 147.3 ± 0.5 | 4.94 ± 0.13 | 109 ± 1 | 24.9 ± 0.6 | 7.51 | 40.1 ± 0.4 |
| Ex. 5 | 147.2 ± 0.6 | 5.01 ± 0.08 | 108 ± 0 | 26.9 ± 0.3 | 7.49 | 40.8 ± 0.3 |
| Ex. 6 | 146.4 ± 1.1 | 5.07 ± 0.14 | 106 ± 1 | 24.7 ± 1.1 | 7.41 | 41.5 ± 1.0 |
| Ex. 7 | 149.5 ± 0.5 | 4.80 ± 0.11 | 109 ± 1 | 25.7 ± 0.5 | 7.49 | 41.6 ± 0.9 |
| Ex. 8 | 148.9 ± 1.3 | 4.98 ± 0.08 | 109 ± 1 | 26.6 ± 0.8 | 7.46 | 40.4 ± 0.7 |
| Ex. 9 | 149.2 ± 0.5 | 5.12 ± 0.10 | 107 ± 1 | 25.1 ± 0.6 | 7.46 | 41.9 ± 0.2 |
| Ex. 10 | 149.5 ± 0.6 | 5.08 ± 0.11 | 107 ± 1 | 26.0 ± 0.8 | 7.41 | 42.2 ± 0.1 |
| Ex. 11 | 149.9 ± 0.5 | 4.50 ± 0.19 | 108 ± 1 | 26.6 ± 0.4 | 7.50 | 40.8 ± 0.6 |
| BES | 152.1 ± 0.3 | 4.24 ± 0.15 | 111 ± 1 | 26.6 ± 0.5 | 7.45 | 40.5 ± 0.2 |
| Golytely | 148.1 ± 1.0 | 4.64 ± 0.08 | 108 ± 1 | 25.5 ± 0.6 | 7.49 | 39.5 ± 0.7 |
| Physiological | 149.5 ± 0.7 | 4.62 ± 0.16 | 119 ± 1 | 17.7 ± 1.0 | 7.30 | 40.8 ± 1.2 |

TABLE 5-continued

| | Serum electrolyte level (mEq/liter) | | | | | Hematocrit |
|---|---|---|---|---|---|---|
| | Na+ | K+ | Cl− | HCO3− | pH | value (%) |
| saline | | | | | | |

Experiment 4

Fifteen healthy men and women aging from 22 to 38 years old drank each 100 ml of the lavage solutions of the present invention prepared in Examples 1, 2, 6, and 11, and Golytely for evaluating the taste thereof.

The evaluation was made by the following questionnaire of four ranks:

(A) Very tasty
(B) Rather tasty
(C) Drinkable with patience
(D) Unsavory and undrinkable The results are shown in Table 6. It was found that the lavage solutions of the present invention had an improved taste and were much more tasty than Golytely.

TABLE 6

| | (Scord No.) | | | | |
|---|---|---|---|---|---|
| | Example No. | | | | |
| | 1 | 2 | 6 | 11 | Golytely |
| A | 0 | 1 | 0 | 0 | 0 |
| B | 15 | 14 | 13 | 11 | 1 |
| C | 0 | 0 | 2 | 4 | 9 |
| D | 0 | 0 | 0 | 0 | 5 |
| Total | 15 | 15 | 15 | 15 | 15 |

What is claimed is:

1. A bowel lavage composition which comprises at least one water-soluble polymer selected from the group consisting of polyethylene glycol, dextran, dextrin, hydroxyethylated starch, polydextrose, arabic gum, pullulan and pectin, present in the amount of 10-150g; a sodium salt of an organic acid, present in the amount of 5-60 mmol; sodium chloride, present in the amount of 7- 60 mmol; and at least one member selected from the group consisting of a potassium salt of an organic acid and potassium chloride, the total potassium ion content of the composition being from 2-12 mEq; wherein the organic acid is selected from the group consisting of acetic acid, lactic acid, citric acid, succinic acid, malic acid and tartaric acid the composition being free of hydrogen carbonate ions.

2. The composition of claim 1 which is dissolved in water.

3. The composition of claim 1, wherein the organic acid is a member of the class consisting of citric acid, succinic acid, malic acid and tartaric acid.

4. The composition of claim 1, wherein the organic acid is citric acid.

5. The composition according to claim 1, further comprising sodium sulfate in an amount of up to 20 mmol.

6. The composition of claim 2, wherein the amount of water is from 1-4 liters.

* * * * *